(12) United States Patent
Kanzaki et al.

(10) Patent No.: US 6,972,289 B1
(45) Date of Patent: Dec. 6, 2005

(54) CELL DIVISION INHIBITOR AND A PRODUCTION METHOD THEREOF

(75) Inventors: Hiroshi Kanzaki, Okayama (JP); Kaneo Kanoh, Kamaishi (JP); Satohiro Yanagisawa, Kobe (JP); Teruhiko Nitoda, Okayama (JP); Kazumi Akazawa, Kurashiki (JP)

(73) Assignee: Nereus Pharmaceuticals, Inc., San Diego, CA (US)

( * ) Notice: Subject to any disclaimer, the term of this patent is extended or adjusted under 35 U.S.C. 154(b) by 258 days.

(21) Appl. No.: 10/181,786

(22) PCT Filed: Sep. 29, 2000

(86) PCT No.: PCT/JP00/06807

§ 371 (c)(1),
(2), (4) Date: Dec. 2, 2002

(87) PCT Pub. No.: WO01/53290

PCT Pub. Date: Jul. 26, 2001

(30) Foreign Application Priority Data

Jan. 18, 2000 (JP) .............................. 2000-009370

(51) Int. Cl.[7] .................. A61K 31/495; C07D 241/02; C07D 403/02; C07D 241/04
(52) U.S. Cl. ...................... 514/253; 514/252; 514/255; 544/357; 544/368; 544/370; 544/385
(58) Field of Search ............................... 514/253, 252, 514/255; 544/357, 368, 370, 385

(56) References Cited

FOREIGN PATENT DOCUMENTS

WO    WO96/20190    *  7/1996  ......... C07D 401/12

OTHER PUBLICATIONS

Akerlund et al., "Diketopiperazine-Based Polymers from Common Amino Acids", ouurnal of Applied Polymer Science (2000), 78 (12), 2213-2218.*
Saito et al, Synthesis of novel octahydro-1, 5-imino-3-benzazocin-4, 7, 10-trione derivatives having a methyl group at the C-2 position as ABC ring models of saframycins. Chemical & Pharmaceutical Bulletin (1997), 45(7), 1120-1129.*

Fukushima et al., "Biological Activities of Albonoursin," *J. Antibiotics,* 26: 175 (1973).
Kanoh et al., "(-)-Phenylahistin: A New Mammalian Cell Cycle Inhibitor Produced by *Aspergillus USTUS,*" *Bioorganic & Medicinal Chemistry Letters,* 7: 2847-2852 (1997).
Kanoh et al., "Synthesis and Biological Activities of Phenylahistin Derivatives," *Bioorganic & Medicinal Chemistry,* 7: 1451-1457 (1999).
Kanoh et al., "Antitumor Activity of Phenylahistin in Vitro and in Vivo," *Bioscience Biotechnology Biochemistry,* 63: 1130-1133 (1999).
Kanoh et al., "(-)-Phenylahistin Arrests Cells in Mitosis by Inhibiting Tubulin Polymerization," *The Journal of Antibiotics,* 52: 134-141 (1999).
Kanzaki et al., "Effective Production of Dehydro Cyclic Dipeptide Albonoursin Exhibiting Pronuclear Fusion Inhibitory Activity," *The Journal of Antibiotics,* 52: 1017-1022 (1999).
Kanzaki et al., *A Summary of the Symposium of the Society for Actinomycetes Japan,* p. 42 (1999).
Kobayashi et al., *A Summary of the Symposium on the Chemistry of Natural Products,* p. 51 (1989).
Kopple et al., "A Convenient Synthesis of 2,5-Piperazinediones[1a]," *The Journal of Organic Chemistry,* 33: 862-864 (1967).
Nitecki et al., "A Simple Route to Sterically Pure Diketopiperazines[1]," *The Journal of Organic Chemistry,* 33: 864-866 (1968).
Sezaki and Shoten, "Drug Delivery Systems", *Drug Development,* 13: 116, Table 2. 29, (Jul. 1989).
Amendment and Response to Written Opinion submitted in International Application No. PCT/US03/024232 on Jan. 20, 2005.

* cited by examiner

*Primary Examiner*—Raymond Richard
*Assistant Examiner*—Paul V. Ward
(74) *Attorney, Agent, or Firm*—Knobbe, Martens, Olson & Bear, LLP

(57) ABSTRACT

The present invention relates to a cell division inhibitor comprising various dehydrodiketopiperazines such as dehydrophenylahistin, or analogs thereof as an active ingredient, and a dehydrogenase and a method for producing the same inhibitor.

9 Claims, No Drawings

CELL DIVISION INHIBITOR AND A PRODUCTION METHOD THEREOF

TECHNICAL FIELD

The present invention relates to a cell division inhibitor (a cell cycle inhibitor) and an antitumor agent, and a method of producing them using enzymes.

BACKGROUND

The growth and differentiation of cells constituting a human body are strictly controlled in order to maintain homeostasis. Cells divide or proliferate by repeating a cell cycle consisting of a certain process comprising M period, G1 period, S period and G2 period. A defect in the control mechanism of this cell cycle results in the development of cancer or immune disease.

Lately, the control mechanism of cell cycle is clarifying at a molecular level, and it is known that a substance controlling a cell cycle possibly can be used as an antitumor agent or an immunosuppressive agent. In recent years, as an antitumor agent or a lead compound thereof, the spotlight has centered on a substance, such as pacritaxel, vincristine or vinblastine, inhibiting the function of tubulin which is one of cytoskeleton proteins playing a major role in precisely distributing a replicated gene into a daughter cell in a cell division stage.

Fukushima et al. have found that albonoursin has an antitumor activity and an antibacterial activity (Fukushima et al., *J. Antibiotics*, Vol. 26, pp. 175, 1973), while Kobayashi et al. have found that albonoursin acts to inhibit the pronuclear fusion between a female nucleus and a male nucleus (Kobayashi et al., *A Summary of the Symposium on the Chemistry of Natural Products*, P51, 1989). Furthermore, Kanzaki et al. have found that tetradehydrocyclo (Phe—Phe) exhibits sea urchin embryo division inhibitory activity (*A Summary of the Symposium of the Society for Actinomycetes Japan*, P42, 1999).

Kanoh et al. have found that, filamentous bacteria, *Aspergillus ustus* NSC-F037 and *Aspergillus ustus* NSC-F038, which were isolated from the soil in Kanagawa prefecture, produce a novel antitumor substance phenylahistin, and have determined the structure of this substance. Phenylahistin molecules have a chiral carbon atom, and as a result of a thorough examination, Kanoh et al. have further discovered that phenylahistin produced by the above bacteria is a mixture of (−)-phenylahistin and (+)-phenylahistin, and that the antitumor acitivity of (−)-phenylahistin is approx. 30–100 times stronger than that of (+)-phenylahistin (Japanese Patent Application Laying-Open (kokai) No. 10-130266, Kanoh et al., *Bioorganic & Medicinal Chemistry Letters*, Vol. 7, No. 22, pp. 2847–2852, 1997; Kanoh et al., *Bioscience Biotechnology Biochemistry*, Vol. 63, No. 6, pp. 1130–1133, 1999). Further, they have found that (−)-phenylahistin inhibits the polymerization of tubulin (Kanoh et al., *The Journal of Antibiotics*, Vol. 52, No. 2, pp. 134–141, 1999). Furthermore, Kanoh et al. have examined the antitumor effect of (−)-phenylahistin, using a cancer cell transplanted model animal, and have shown that (−)-phenylahistin has a certain degree of antitumor activity (Kanoh et al., *Bioscience Biotechnology Biochemistry*, Vol. 63, No. 6, pp. 1130–1133, 1999). From a clinical position, however, an agent having a stronger antitumor activity than (−)phenylahistin is desirable.

DISCLOSURE OF THE INVENTION

The object of the present invention is to provide a cell division inhibitor having a stronger cell cycle inhibitory activity, particularly antitumor activity, and a method of producing the inhibitor using enzymes.

As a result of thorough analysis by the present inventors to achieve the above object, it has been found that various dehydrodiketopiperazines such as dehydrophenylahistin or affinities thereof have a stronger cell cycle inhibitory activity than (−)-phenylahistin, and have completed the present invention.

That is to say, the present invention comprises each of the following inventions.

(1) A cell division inhibitor comprising, as an active ingredient, a compound of formula (I) or pharmaceutically acceptable salt thereof:

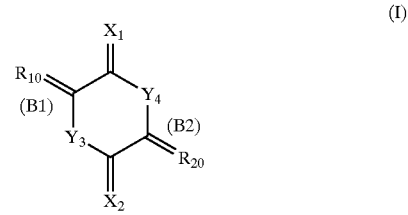

(I)

wherein
each of $X_1$ and $X_2$ is independently oxygen or sulfur;
$Y_3$ is oxygen, sulfur, —$NR_3$— or —$CR_{31}R_{32}$—;
$Y_4$ is oxygen, sulfur, —$NR_4$— or —$CR_{41}R_{42}$—;
$R_{10}$ is halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_{10}$ may be branched or cyclized, or may comprise a heteroatom;
$R_{20}$ is halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_{20}$ may be branched or cyclized, or may comprise a heteroatom;
each of $R_3$ and $R_4$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;
each of $R_{31}$, $R_{32}$, $R_{41}$ and $R_{42}$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;
$R_{10}$ and any of $R_3$, $R_{31}$ and $R_{32}$ may form a ring;
$R_{20}$ and any of $R_4$, $R_{41}$ and $R_{42}$ may form a ring;
each of (B1) and (B2) independently represents a carbon—carbon single bond or a carbon—carbon double bond, wherein at least one represents a carbon—carbon double bond with E or Z configuration;
at least one of the above groups may have a protecting group capable of decomposing in vivo, except in the case where each of $X_1$ and $X_2$ is oxygen, each of $Y_3$ and $Y_4$ is —NH—, $R_{10}$ is benzyl, each of (B1) and (B2) is a carbon—carbon double bond, and $R_{20}$ is isobutyl or benzyl, and in the case where each of $X_1$ and $X_2$ is oxygen, each of $Y_3$ and $Y_4$ is —NH—, $R_{10}$ is benzyl, (B1) is a carbon—carbon single bond, (B2) is a carbon—carbon Z double bond, and $R_{20}$ is a group shown in the following formula (a):

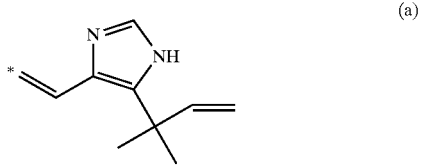

(a)

wherein * represents a bonding position.

(2) The cell division inhibitor according to item 1 above wherein, in the formula (I), each of (B1) and (B2) is a carbon—carbon double bond.

(3) The cell division inhibitor according to item 1 or 2 above wherein, in the formula (I), each of $X_1$ and $X_2$ is oxygen, $Y_3$ is —$NR_3$—, and $Y_4$ is —$NR_4$—.

(4) The cell division inhibitor according to item 3 above wherein, in the formula (I), each of $Y_3$ and $Y_4$ is —NH—.

(5) A cell division inhibitor comprising, as an active ingredient, a compound of formula (II) or an E form thereof, or pharmaceutically acceptable salt thereof:

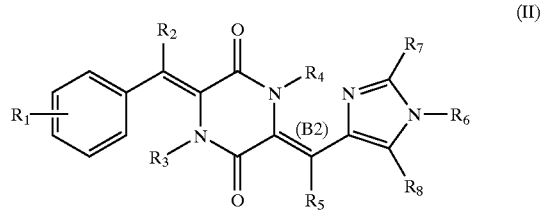

(II)

wherein $R_1$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_1$ may be branched or cyclized, or may comprise a heteroatom, and further $R_1$ may be one atom or group, or at most 5 identical or different atoms or groups, and the atoms or groups may mutually form a ring;

$R_2$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_2$ may be branched or cyclized, or may comprise a heteroatom;

each of $R_3$ and $R_4$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;

$R_5$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_5$ may be branched or cyclized, or may comprise a heteroatom;

$R_6$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_6$ may be branched or cyclized, or may comprise a heteroatom;

each of $R_7$ and $R_8$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;

$R_2$ and $R_3$ may form a ring;

$R_4$ and any of $R_5$, $R_6$, $R_7$ and $R_8$ may form a ring;

(B2) represents a carbon—carbon single bond or a carbon—carbon double bond;

at least one of the above groups may have a protecting group capable of decomposing in vivo.

(6) The cell division inhibitor according to item 5 above wherein, in the formula (II), (B2) is a carbon—carbon double bond.

(7) The cell division inhibitor according to item 6 above wherein, in the formula (II), at least one of $R_7$ and $R_8$ is 1,1-dimethyl-2-propenyl.

(8) The cell division inhibitor according to any one of items 1–7 above wherein it is an antitumor agent.

(9) A dehydrogenase which has an activity to convert a compound represented by the above formula (I) wherein at least one of (B1) and (B2) is a carbon—carbon single bond, or by the above formula (II) wherein (B2) is a carbon—carbon single bond into a compound wherein the carbon—carbon single bond(s) is replaced with a carbon—carbon double bond(s).

(10) The dehydrogenase according to item 9 above whose molecular weight is 700–800 kDa.

(11) The dehydrogenase according to item 9 or 10 above which is produced by *Streptomyces albulus*.

(12) A method of producing the cell division inhibitor according to any one of items 1–8 above, which comprises using, as a substrate, a compound represented by the above formula (I) wherein at least one of (B1) and (B2) is a carbon—carbon single bond, or a compound represented by the above formula (II) wherein (B2) is a carbon—carbon single bond, and converting the carbon—carbon single bond to a carbon—carbon double bond by use of a cell, cell-free extract or enzyme solution containing the dehydrogenase according to any one of items 9–11 above.

(13) The method according to item 12 above wherein the dehydrogenase of item 11 above is used.

(14) A compound of formula (II) or an E form thereof, or pharmaceutically acceptable salt thereof:

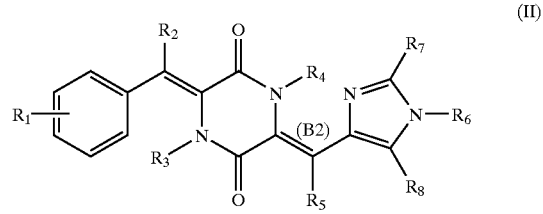

(II)

wherein $R_1$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_1$ may be branched or cyclized, or may comprise a heteroatom, and further $R_1$ may be one atom or group, or at most 5 identical or different atoms or groups, and the atoms or groups may mutually form a ring;

$R_2$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_2$ may be branched or cyclized, or may comprise a heteroatom;

each of $R_3$ and $R_4$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;

$R_5$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_5$ may be branched or cyclized, or may comprise a heteroatom;

$R_6$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_6$ may be branched or cyclized, or may comprise a heteroatom;

each of $R_7$ and $R_8$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;

$R_2$ and $R_3$ may form a ring;

$R_4$ and any of $R_5$, $R_6$, $R_7$ and $R_8$ may form a ring;

(B2) represents a carbon—carbon single bond or a carbon—carbon double bond;

at least one of the above groups may have a protecting group capable of decomposing in vivo.

The details of the present invention are disclosed below.

First of all, regarding various definitions which the present invention comprises, appropriate examples and explanations are provided below.

The term "halogen" appearing in the formulas (I) and (II) means fluorine, chlorine, bromine or iodine, unless otherwise specified.

$C_{1-25}$ alkyl represented by $R_1$, $R_2$, $R_3$, $R_4$, $R_5$, $R_6$, $R_7$, $R_8$, $R_{10}$, $R_{20}$, $R_{31}$, $R_{32}$, $R_{41}$ or $R_{42}$ is an alkyl group having 1 to 25 carbon atoms, which may be normal-chained, branched or cyclized. Examples of $C_{1-25}$ alkyl include methyl, ethyl, propyl, isopropyl, cyclopropyl, butyl, isobutyl, tert-butyl, pentyl, isopentyl, cyclopentyl, hexyl, cyclohexyl, heptyl, 5-methylhexyl, cycloheptyl, octyl, 6-methylheptyl, nonyl, 7-methyloctyl, decyl and 8-methylnonyl, preferably $C_{1-10}$ alkyl, and more preferably $C_{1-6}$ alkyl. These alkyl groups may be substituted with other substituent(s), and may comprise a heteroatom such as halogen, oxygen, sulfur, nitrogen or the like.

$C_{2-25}$ alkenyl represented by $R_1$, $R_2$, $R_3$, $R_4$, $R_5$, $R_6$, $R_7$, $R_8$, $R_{10}$, $R_{20}$, $R_{31}$, $R_{32}$, $R_{41}$ or $R_{42}$ is an alkenyl group having 2 to 25 carbon atoms, which may be normal-chained, branched or cyclized. Examples of $C_{2-25}$ alkenyl include vinyl, propenyl, 1,1-dimethyl-2-propenyl and 3-methyl-3-butenyl, preferably $C_{2-10}$ alkenyl, and more preferably $C_{2-6}$ alkenyl. These alkenyl groups may be substituted with other substituent(s), and may comprise a heteroatom such as halogen, oxygen, sulfur, nitrogen or the like.

$C_{2-25}$ alkynyl represented by $R_1$, $R_2$, $R_3$, $R_4$, $R_5$, $R_6$, $R_7$, $R_8$, $R_{10}$, $R_{20}$, $R_{31}$, $R_{32}$, $R_{41}$ or $R_{42}$ is an alkynyl group having 2 to 25 carbon atoms, which may be normal-chained, branched or cyclized. Examples of $C_{2-25}$ alkynyl include ethynyl, propynyl and butynyl, preferably $C_{2-10}$ alkynyl, and more preferably $C_{2-6}$ alkynyl. These alkenyl groups may be substituted with other substituent(s), and may comprise a heteroatom such as halogen, oxygen, sulfur, nitrogen or the like.

$C_{1-25}$ alkoxy represented by $R_1$, $R_2$, $R_3$, $R_4$, $R_5$, $R_6$, $R_7$, $R_8$, $R_{10}$, $R_{20}$, $R_{31}$, $R_{32}$, $R_{41}$ or $R_{42}$ is an alkoxy group having 1 to 25 carbon atoms, which may be normal-chained, branched or cyclized. Examples of $C_{1-25}$ alkoxy include methoxy, ethoxy, propoxy, isopropoxy, butoxy, isobutoxy, tert-butoxy, pentyloxy, isopentyloxy, cyclopentyloxy, hexyloxy, cyclohexyloxy, heptyloxy, 5-methylhexyloxy, cycloheptyloxy, octyl, 6-methylheptyloxy, nonyloxy, 7-methyloctyloxy, decyloxy and 8-methylnonyloxy, preferably $C_{1-10}$ alkoxy, and more preferably $C_{1-6}$ alkoxy. These alkoxy groups may be substituted with other substituent(s), and may comprise a heteroatom such as halogen, oxygen, sulfur, nitrogen or the like.

Aryl represented by $R_1$, $R_2$, $R_3$, $R_4$, $R_5$, $R_6$, $R_7$, $R_8$, $R_{10}$, $R_{20}$, $R_{31}$, $R_{32}$, $R_{41}$ or $R_{42}$ is a monocyclic or polycyclic aromatic hydrocarbon group, and examples include phenyl, naphthyl and anthranyl, but preferably phenyl. These aryl groups may be substituted with other substituent(s) such as $C_{1-6}$ alkyl (preferably methyl, ethyl and propyl), $C_{1-6}$ alkoxy, halogen, nitro, amino, carboxyl, hydroxy-$C_{1-6}$ alkyl, hydroxyl or protected hydroxyl, and may comprise a heteroatom such as oxygen, sulfur, nitrogen or the like as a ring forming member.

Aralkyl represented by $R_1$, $R_2$, $R_3$, $R_4$, $R_5$, $R_6$, $R_7$, $R_8$, $R_{10}$, $R_{20}$, $R_{31}$, $R_{32}$, $R_{41}$ or $R_{42}$ is $C_{1-6}$ alkyl substituted with the above aryl, and examples include benzyl, phenethyl, naphthylmethyl and anthranylmethyl, but preferably benzyl. These aralkyl groups may be substituted with other substituent(s) such as $C_{1-6}$ alkyl (preferably methyl, ethyl and propyl), $C_{1-6}$ alkoxy, halogen, nitro, amino, carboxyl, hydroxy-$C_{1-6}$ alkyl, hydroxyl or protected hydroxyl, and may comprise a heteroatom such as oxygen, sulfur, nitrogen or the like as a ring forming member.

The examples of substituents in substituted amino represented by $R_1$, $R_2$, $R_3$, $R_4$, $R_5$, $R_6$, $R_7$, $R_8$, $R_{10}$, $R_{20}$, $R_{31}$, $R_{32}$, $R_{41}$ or $R_{42}$ include $C_{1-6}$ alkyl, $C_{1-6}$ alkoxy, halogen, carboxyl, hydroxy-$C_{1-6}$ alkyl, hydroxyl or protected hydroxyl.

In the above formula (I), $R_{10}$ and any of $R_3$, $R_{31}$ and $R_{32}$ may form a ring, and $R_{20}$ and any of $R_4$, $R_{41}$ and $R_{42}$ may form a ring. In the above formula (II), $R_2$ and $R_3$ may form a ring, and $R_4$ and any of $R_5$, $R_6$, $R_7$ and $R_8$ may form a ring.

As $C_{2-25}$ alkenyl represented by $R_7$ or $R_8$, an alkenyl group corresponding to an isoprene unit consisting of 5 carbon atoms, that is, 1,1-dimethyl-2-propenyl or 3-methyl-3-butenyl, and an alkenyl group consisting of two or more isoprene units, preferably at most 3 isoprene units (up to 15 carbon atoms) are desirable.

Substituents appearing in the above formulas (I) and (II) may have a protecting group capable of, decomposing in vivo. Among these protecting groups, as a protecting group for an amino group for example, there may be used a protecting group having the binding form such as acid amide, carbamate and the like which are described in *Drug Development* vol. 13, "Drug Delivery Systems" edited by Hitoshi SEZAKI, Hirokawa Shoten (July 1989), page 116, Table 2. 29, but an acyl such as acetyl derived from fatty acid is preferable.

The double bond of a compound shown in the above formulas (I) or (II) may be either in Z configuration or in E configuration, but preferably in Z configuration.

In the case where (B 1) and/or (B2) is a carbon—carbon double bond, the above substituent binding to the above carbon—carbon double bond becomes a corresponding divalent group. For example, methyl becomes methylene, and benzyl becomes phenylmethylene (benzylidene).

Among possible compounds represented by the above formula (I), a compound wherein each of $X_1$ and $X_2$ is oxygen, each of $Y_3$ and $Y_4$ is —NH—, $R_{10}$ is benzyl, each of (B1) and (B2) is a carbon—carbon double bond, and $R_{20}$ is isobutyl (the common name: albonoursin, the compound name: 3-(Z)-benzylidene-6-(Z)isobutylidene-2,5-piperazine dione) refers to the known antitumor agent described in Fukushima et al., *J. Antibiotics*, Vol. 26, pp. 175, 1973) and the known pronuclear fusion inhibitory agent described in *A Summary of the Symposium on the Chemistry of Natural Products*, P51, 1989, and these two agents are excluded from the cell division inhibitor of the present invention. In addition, a compound (tetradehydrocyclo (Phe—Phe)) wherein each of $X_1$ and $X_2$ is oxygen, each of $Y_3$ and $Y_4$ is —NH—, each of $R_{10}$ and $R_{20}$ is benzyl, and each of (B1) and (B2) is a carbon—carbon double bond refers to the known sea urchin embryo division inhibitory agent described in *A Summary of the Symposium of the Society for Actinomycetes Japan*, P42, 1999, and this agent is excluded from the cell division inhibitor of the present invention. Furthermore, a compound (the common name: phenylahistin, the compound name: 3-{[5-(1,1-dimethyl-2-propenyl)imidazole-4-yl]methylene}-6-benzylpiperazine-2,5-dione) wherein each of $X_1$ and $X_2$ is oxygen, each of $Y_3$ and $Y_4$ is —NH—, $R_{10}$ is benzyl, (B1) is a carbon—carbon single bond, (B2) is a carbon—carbon Z double bond, and $R_{20}$ is a group shown in the following formula (a):

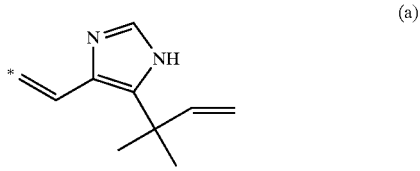

(a)

(wherein * represents a bonding position)

is the known cell division inhibitor disclosed in Japanese Patent Application Laying-Open (kokai) No. 10-130266 and so on, and this agent is excluded from the cell division inhibitor of the present invention. Generally, a compound wherein, in the above formula (I), each of $X_1$ and $X_2$ is independently oxygen or sulfur, $Y_3$ is —$NR_3$—, $Y_4$ is —$NR_4$— (herein $R_3$ and $R_4$ are defined as with stated above), $R_{10}$ is substituted or unsubstituted benzyl, (B1) is a carbon—carbon single bond, (B2) is a carbon—carbon Z double bond, and $R_{20}$ is substituted or unsubstituted imidazole-4-ylmethylene is excluded from those used for the cell division inhibitor of the present invention.

Further, in the above formula (I), a compound wherein (B1) is a carbon—carbon double bond and (B2) is a carbon—carbon single bond or a carbon—carbon double bond is preferable, and a compound wherein each of (B1) and (B2) is a carbon—carbon double bond is more preferable.

Preferable examples of compounds shown in the above formulas (I) and (II) include 3-(imidazole-4-ylmethylene)-6-(phenylmethylene)piperazine-2,5-dione; 3-[(5-methylimidazole-4-yl)methylene]-6-(phenylmethylene)piperazine-2,5-dione; 3-[(5-ethylimidazole-4-yl)methylene]-6-(phenylmethylene)piperazine-2,5-dione; 3-[(5-butylimidazole-4-yl)methylene]-6-(phenylmethylene) piperazine-2,5-dione; 3-[(5-pentylimidazole-4-yl) methylene]-6-(phenylmethylene)piperazine-2,5-dione; 3-{[5-(1,1-dimethyl-2-propenyl)imidazole-4-yl]methylene}-6-(phenylmethylene) piperazine-2,5-dione.

Pharmaceutically acceptable salt of a compound shown in the above formula (I) or (II) is ordinary organic or inorganic atoxic salt. In the case where the above compound is a basic substance, the salts that are preferably used are hydrochloride, hydrobromide, sulfate, nitrate, acetate, methanesulfonate and toluenesulfonate, and in the case where the compound is an acidic substance, the salt that is preferably used is a salt with inorganic base including alkali metallic salt (e.g. sodium salt, potassium salt etc.) and alkali-earth metallic salt (e.g. calcium salt, magnesium salt etc.) The term "pharmaceutically acceptable" in the present specification means that the salt is not only acceptable in medical agents, veterinary agents, agricultural chemicals, antimicrobial agents, insecticides etc., but also in a field comprising reagents used for study purposes.

The cell division inhibitor of the present invention can be used for the purpose of inhibiting the cell division, cell cycle and pronuclear fusion between a female nucleus and a male nucleus of a procaryote or an eucaryote. Specifically, the cell division inhibitor of the present invention is useful as an antimicrobial agent, agricultural chemical, veterinary agent, insecticide, medical agent and reagent for study purposes. Furthermore, among medical agents, it is particularly useful as an antitumor agent. The cell division inhibitor of the present invention is effective in a pathological condition wherein cell divisions are disorderly repeated. It is particularly useful for cancers, and also effective in a pathological condition appearing in a certain type of autoimmune disease, chronic articular rheumatism etc., where a certain type of cell continues to grow disorderly.

Furthermore, the antitumor agent of the present invention can comprise other pharmaceutically effective ingredients, i.e., other antitumor agents as necessary as well as the above active ingredients in order to treat various diseases. When the antitumor agent takes the form of granule, fine granule, powder, tablet or capsule, it is preferable that the antitumor agent comprises 5–80 weight % of the above active ingredients. When the antitumor agent takes a liquid form, it is preferable that the antitumor agent comprises 1–30 weight % of the above active ingredients. Further, when the antitumor agent is used as an injection among parenteral agents, it is preferable that the inhibitor comprises 1–10 weight % of the above active ingredients.

For use in oral administration, the applied dose of the above active ingredients is preferably 0.1 mg to 1 g per day per adult. However, depending on the age, body weight, symptom etc. of a patient, the dose can be changed as appropriate. The antitumor agent of the present invention can be administered once per day, but also it can be dividedly administered twice or three times at regular time intervals. When it is used as an injection, the applied dose of the above active ingredients is preferably 1 to several hundreds of milligrams per administration per adult. Moreover, it is possible to administer 1–3 times per day or once every 2 or 3 days by injection, or to administer sustainably by drip infusion or the like.

As a substrate of the dehydrogenase of the present invention comprises a compound wherein, in the above formula (I), at least one of (B1) and (B2) is a carbon—carbon single bond, or a compound wherein, in the above formula (II), (B2) is a carbon—carbon single bond can be used, but preferably a compound wherein, in the above formula (I), each of $X_1$ and $X_2$ is oxygen, $Y_3$ is —$NR_3$—, and $Y_4$ is —$NR_4$— (herein $R_3$ and $R_4$ are defined as with stated above), more preferably a compound wherein, in the above formula (I), each of $X_1$ and $X_2$ is oxygen, and each of $Y_3$ and $Y_4$ is —NH— is used, and further more preferably a cyclic dipeptide wherein two amino acids of L form condense to form a diketopiperazine ring or substituted compounds thereof is used. Examples of the above condensing amino acids preferably include cyclic (aromatic) amino acids such as phenylalanine, histidine, tryptophan and tyrosine. Examples of substituents in the substituted compounds of the above cyclic dipeptide include halogen, $C_{1-25}$ alkyl, $C_{2-25}$ alkenyl, $C_{2-25}$ alkynyl, $C_{1-25}$ alkoxy, aralkyl, hydroxyl, amino, nitro and aryl. These substituents may be substituted with other substituent(s), and a part of the carbon chain may be branched or cyclized, may comprise a heteroatom, may mutually form a ring, and may have a protecting group capable of decomposing in vivo. The substituents include preferably $C_{2-6}$ alkyl or $C_{2-6}$ alkenyl, more preferably 1,1-dimethyl-2-propenyl.

The majority of compounds used as the substrate stated above are the known compounds (Japanese Patent Application Laying-Open (kokai) No. 10-130266; Kanoh et al., *Biorganic &Medicinal Chemistry Letters*, Vol. 7, No. 22, pp. 2847–2852, 1997; Kanoh et al., *Bioscience Biotechnology Biochemistry*, Vol. 63, No. 6, pp. 1130–1133, 1999; Kanoh et al., *Bioorganic & Medicinal Chemistry*, Vol. 7, pp. 1451–1457, 1999), and these compounds are available. Other compounds can be produced by the same methods as those described in Kopple et al., *The Journal of Organic Chemistry*, Vol. 33, pp. 862–864, 1968 or Nitecki et al., *The Journal of Organic Chemistry*, Vol. 33, pp. 864–866, 1968.

The dehydrogenase of the present invention includes molecules having a variety of molecular weights, but one whose molecular weight is 700–800 kDa is preferable.

The present invention can use, as a coenzyme of the dehydrogenase, synthetic compounds such as dichlorophenolindophenol (DCIP), phenazine methosulfate (PMS), ferricyanide, tetramethylphenylenediamine and quinones, as well as natural compounds such as nicotin adenine dinucleotide (NAD), nicotin adenine dinucleotide phosphate (NADP), flavine adenine dinucleotide (FAD), flavin mononucleotide (FMN), pyrrolo-quinoline quinone (PQQ) and cytochromes. However, among them, FMN, PQQ, cytochromes, DCIP, PMS, ferricyanide, tetramethylphenylenediamine and quinones are preferable, and DCIP and/or PMS are further preferable.

The dehydrogenase of the present invention may be obtained from any organism, but ones derived from microorganisms such as bacteria, actinomycetes and filamentous fungi are preferable, ones from actinomycetes are more preferable, and ones from *Streptomyces albulus* are even more preferable.

The dehydrogenase from *Streptomyces albulus* has the following physicochemical properties:

(i) Function: The dehydrogenase from *Streptomyces albulus* acts to convert a carbon—carbon single bond on the position 3 or 6 into a carbon—carbon double bond.

(ii) Substrate specificity: The dehydrogenase from *Streptomyces albulus* converts phenylahistin into dehydrophenylahistin, and converts cyclophenylalanylhistidyl into dehydrocyclophenylalanylhistidyl or tetradehydrocyclophenylalanylhistidyl.

(iii) Optimum pH: 8.3
(iv) pH stability: stable at 7.0–9.0
(v) Optimum temperature: 60° C.
(vi) Heat stability: stable at 20–70° C., deactivated at 80° C.
(vii) Molecular weight: 700 kDa-800 kDa The dehydrogenase of the present invention may be used not only as a natural tissue or cell, but also as a cell-free extract or enzyme solution obtained by partially or fully purifying the cell-free extract. The dehydrogenase may be purified according to the common enzyme purification method. Also, the multi-step reactions may be carried out at one time by mixing other enzymes.

The dehydrogenase of the present invention can produce a compound wherein, in the above formula (I), at least one of (B1) and (B2) is a carbon—carbon double bond or a compound wherein, in the above formula (II), (B2) is a carbon—carbon double bond, by using as a substrate a compound wherein, in the above formula (I), at least one of (B1) and (B2) is a carbon—carbon single bond, or a compound wherein, in the above formula (II), (B2) is a carbon—carbon single bond. And these compounds are useful as a cell division inhibitor or an antitumor agent.

Some examples are provided below to describe the present invention more specifically.

The active ingredient of the cell division inhibitor of the present invention is a substance wherein, in the above formula (I), at least one of (B1) and (B2) is a carbon—carbon double bond, and representative examples include substituted or non-substituted dehydrodiketopiperazines, substituted or non-substituted tetradehydrodiketopiperazines, substituted or unsubstituted dehydro-cyclic dipeptide, substituted or unsubstituted tetradehydro-cyclic dipeptide, particularly substituted or unsubstituted dehydro-cyclophenylalanylhistidyl or tetradehydrocyclophenylalanylhistidyl represented by the above formula (II), and further particularly dehydrophenylahistin.

As an example, the method of producing dehydrophenylahistin is provided below, but needless to say, the present invention is not limited thereto.

The method of collecting a novel compound dehydrophenylahistin by culturing an actinomycete, for example, *Streptomyces albulus* KO23 (which was deposited with the National Institute of Bioscience and Human-Technology, Agency of Industrial Science and Technology (Higashi 1-1-3, Tsukuba-shi, Ibaragi-ken, Japan) under accession No. FERM BP-6994 on Jan. 14, 2000), preparing a dehydrogenase from the culture, and allowing it to act on phenylahistin is specifically described later. But, as a dehydrogenase, either a purified enzyme or a natural cell extract may be used. Generally, the dehydrogenase can be prepared according to the method of culturing an actinomycete belonging to the genus *Streptomyces*. After the culture, in order to purify the dehydrogenase of the present invention from the culture solution or prepare a cell extract containing the enzyme activity, generally a common method used to purify the enzyme derived from microorganism can be applied as appropriate. For example, methods such as ultrasonic disintegration, centrifugation, salting out, dialysis, various ion exchange resin methods, nonionic adsorption method, chromatography including gel filtration chromatography, high performance liquid chromatography, crystallization or freeze-drying can be applied separately, in combination as appropriate, or repeatedly.

The method of carrying out dehydrogenation reaction by using an enzyme solution or cell extract prepared as above is specifically described in the Examples later, but the fact is that an enzyme solution and a substrate phenylahistin thereof are mixed to react in buffer such as a phosphate buffer. If necessary, it is possible to add an organic solvent to the reaction solution.

In order to purify and isolate dehydrophenylahistin from the above reaction solution, generally a common method of isolating/purifing organic compounds is applied as appropriate. For example, methods such as various ion exchange resin methods and nonionic adsorption methods; gel filtration chromatography, chromatography with adsorbents including activated carbon, alumina, silica gel etc., and high performance liquid chromatography; crystallization; vacuum concentration; or freeze-drying can be applied separately, in combination as appropriate, or repeatedly.

Dehydrophenylahistin produced by the above method has cell division inhibitory activity, as disclosed in Examples later. The usage, dosage form and applied dose (usage) of the cell division inhibitor of the present invention comprising dehydrophenylahistin as an active ingredient are determined as appropriate depending on the intended use. For example, in the case of the antitumor agent of the present invention comprising dehydrophenylahistin as an active ingredient, it may be administered either orally or parenterally. Examples of the dosage forms include oral preparations such as a tablet, powder, capsule, granule, extract and syrup, or parenteral preparations such as an injection or suppository. These formulations are produced using pharmaceutically acceptable additives such as an excipient or binder according to known methods. The applied dose of the antitumor agent containing the above dehydrophenylahistin as an active ingredient depends on the age, body weight, susceptibility, and symptoms of a patient. However, the effective amount is generally about 0.1 mg to 1 g per day per adult, and it is also possible to administer just once per day or devidedly several times per day. Furthermore, a dose beyond the above normal limits may be also administered as needed.

When the agent is used as a reagent for a biochemical examination, the development of the cell cycle is inhibited at the G2/M period, if the agent is dissolved in an organic solvent or hydrous organic solvent and administered directly to various cultured cell systems. Examples of the applicable organic solvents include methanol, dimethylsulfoxide etc. Examples of the dosage forms include solid agents such as powder or granule, liquid agents dissolved in organic solvent or hydrous organic solvent, and the like. Generally, an effective amount of the cell division inhibitor comprising the above dehydrophenylahistin as an active ingredient is 0.01–100 µg/mL, but the appropriate amount depends on the type of cultured cell system or intended use. Further, an amount beyond the above normal limits may be also administered as needed.

This specification includes part or all of the contents as disclosed in the specification of Japanese Patent Application No. 2000-9370 which is a priority document of the present application.

BEST MODE FOR CARRYING OUT THE INVENTION

The present invention will be further described in the following examples. In the following examples, cyclo $(A_1—A_2)$, which is a cyclic dipeptide formed by condensation of two amino acids $A_1$ and $A_2$ into a diketopiperazine ring, is designated $CA_1A_2$ ($A_1$ and $A_2$ represent amino acids in single-letter notation, respectively). All of the cyclic dipeptides $CA_1A_2$ are LL-isomers unless otherwise specified. A D-amino acid is designated, for example, $DA_1$, if necessary. Further, dehydro-peptides are designated Δ, so that $C\Delta A_1A_2$ represents cyclo($\Delta A_1—A_2$), $CA_1\Delta A_2$ represents cyclo($A_1—\Delta A_2$), $C\Delta A_1\Delta A_2$ represents cyclo ($\Delta A_1—\Delta A_2$), and $\Delta CA_1A_2$ represents a mixture of $C\Delta A_1A_2$, $CA_1\Delta A_2$ and $C\Delta A_1\Delta A_2$. Furthermore, PLH represents phenylahistin.

EXAMPLE 1

(1) Phenylahistin was prepared as follows.

Phenylahistin-producing bacterial cells (Aspergillus ustus NSC-F038, which was deposited with the National Institute of Bioscience and Human-Technology, Agency of Industrial Science and Technology (Higashi 1-1-3, Tsukuba-shi, Ibaragi-ken, Japan) under accession No. FERM P-15830 on Sep. 3, 1996), were inoculated onto five spots on a solid medium (20 ml per 9 cm dish) which contains 0.5% glucose, 2% glycerol, 0.2% yeast extract, 2% Pharmamedia (cottonseed cake), 0.25% sodium chloride and 1.5% agar (pH 6.5). The cells were then cultured at 26° C. for 7 days in the dark to obtain a spore suspension. The resulting spore suspension (0.1 ml) was inoculated onto each of 400 dishes containing 20 ml of the above solid medium, and then cultured at 26° C. for 8 days in the dark. The resulting culture was crushed using a mixer, and after addition of 8 L ethyl acetate, was allowed to stand for 2 days then extracted. The collected ethyl acetate layer was concentrated under vacuum to obtain 15 g brown syrup. This syrup was dissolved in 20 ml ethyl acetate and applied to a silica gel column (8 cm in diameter, 20 cm in length) prepared with 1:6 acetone-ethyl acetate, followed by elution with 1:6 acetone-ethyl acetate. The eluted solution was fractionated into 500 ml fractions in order of elution. Phenylahistin was contained in the fifth to tenth fractions, which were then concentrated under vacuum to obtain 4.7 g dark brown powder in total. This dark brown powder was dissolved in 10 ml chloroform and applied to a silica gel column (4 cm in diameter, 30 cm in length) prepared with chloroform, followed by elution with 500 ml chloroform and then 50:1 chloroform-methanol. The compound of interest was eluted with 50:1 chloroform-methanol to obtain 1.05 g brown powder in total. After addition of 100 ml ethyl acetate, this brown powder was mixed well and allowed to stand for 2 days to separate out 628 mg phenylahistin as white powder.

(2) Culture of Streptomyces albulus KO23 and preparation of a cell-free extract were carried out as follows.

Ten milliliters of sterilized water containing 50–200 µl surfactant (Triton X-100) was added to and mixed with a slant on which gray spores had formed well, thereby obtaining a spore suspension. This suspension was diluted 1000-fold in a culture medium and cultured under the following conditions. The culture medium had the composition shown in Table 1.

TABLE 1

| KP medium composition (g/L) | |
|---|---|
| Glucose | 15 |
| Glycerol | 10 |
| Polypepton | 10 |
| Beef extract | 10 |
| CaCO$_3$ | 4 |
| | pH 7.3 |

Table 2 shows the culture conditions.

TABLE 2

Culture conditions

Pre-culture in 200 ml Erlenmeyer flask

| | |
|---|---|
| KP medium | 40 ml |
| Culture period | 24 hours |
| Rotation speed | 180 rpm |
| Temperature | 28° C. |

Main culture in 5 L jar fermenter

| | |
|---|---|
| KP medium | 3 L |
| Antifoaming agent (Antiform AFI emulsion) | 10 g per 3 L |
| Culture period | 48 hours |
| Rotation speed | 300 rpm |
| Ventilation volume | 2 L per 3 min |
| Temperature | 28° C. |

The cell-free extract was prepared as follows.

The culture solution (40 ml) was centrifuged at 20,000×g for 15 min at 4° C. to collect the cells. These cells were suspended in 40 ml physiological saline, and then centrifuged again at 20,000×g for 15 min at 4° C. to wash the cells. These cells were suspended in 7.3 ml sodium phosphate buffer (10 mM, pH 8.0), followed by ultrasonication (150 W, 1.5 min, KUBOTA INSONATOR 201M). The resulting solution was centrifuged at 20,000×g for 15 min at 4° C. to obtain the supernatant as a cell-free extract.

(3) Conversion reaction of phenylahistin into dehydrophenylahistin and purification of the reaction product were carried out as follows.

The reaction mixture had the composition shown in Table 3.

TABLE 3

Reaction mixture composition

| | |
|---|---|
| Phenylahistin | 0.5 mg/ml |
| Dimethyl sulfoxide | 10% (v/v) |
| Sodium phosphate buffer (pH 8.0) | 9 mM |
| Cell-free extract | 0.145 units/ml |
| Temperature | 50° C. |

The above reaction mixture (100 ml) was divided into 200 ml Erlenmeyer flasks to contain 20 ml reaction mixture in each flask. The reaction was carried out at 160 strokes/min for 24 hours, followed by centrifugation at 20,000×g for 15 min at 4° C. to obtain a yellow precipitate. This precipitate was dissolved in 55 ml methanol, and then centrifuged again at 20,000×g for 15 min at 4° C. The resulting supernatant was vacuumed-concentrated and dried to a solid, followed by recrystallization from methanol, thereby obtaining 5.58 mg dehydrophenylahistin as a yellow needle crystal.

The resulting dehydrophenylahistin has the following physicochemical data:
EIMS m/z: 348 (M$^+$, 100), 133 (25), 160 (17), 260 (16).
UV (MeOH) 1max, nm (e): 205 (16600), 363 (35300).
$^1$H-NMR (500 MHz, CDCl$_3$):
δ 1.51, 6H, s
δ 5.16, 1H, d (J=17.4)
δ 5.20, 1H, d (J=10.7)
δ 6.03, 1H, dd (J=10.7, 17.4)
δ 6.96, 1H, s
δ 6.98, 1H, s
δ 7.32, 1H, d (J=7.0)
δ 7.37, 2H, d (J=7.3)
δ 7.43, 2H, dd (J=7.0, 7.3)
δ 7.57, 1H, s
δ 8.04, 1H, s
δ 9.06, 1H, br s
δ 12.23, 1H, s The resulting product was identified as (Z, Z)-dehydrophenylahistin based on NOE observed between a proton of diketopiperazine (δ 8.04, 1H, s) and protons of phenyl group (d 7.43, 2H, dd (J=7.0, 7.3)). It has the following structural formula (III):

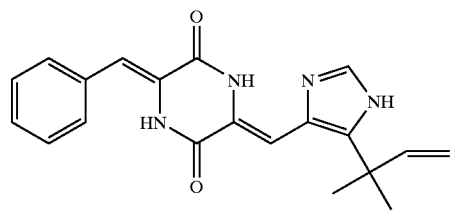

(III)

EXAMPLE 2

Dehydro-products of cyclophenylalanylhistidyl (CFH) were prepared from CFH through dehydrogenation as follows.

TABLE 4

Reaction mixture composition

| | |
|---|---|
| CFH | 0.5 mg/ml |
| Dimethyl sulfoxide | 10% (v/v) |
| Sodium phosphate buffer (pH 8.0) | 9 mM |
| Cell-free extract from Example 1 | 0.435 units/ml |

The reaction mixture (100 ml) shown in Table 4 was prepared and divided into five 20 ml Erlenmeyer flasks. The reaction was carried out in Reciprocal (160 strokes/min) at 50° C. for 24 hours. After 24 hours, the reaction mixture was centrifuged at 20,000×g for 15 min at 4° C. to obtain the supernatant. This supernatant was extracted with ethyl acetate, and then purified by HPLC (Waters 600 Controller, 486 Tunable Absorbance Detector, 616 Pump, Inertsil ODS-3 column φ 20 mm×250 mm, 60% methanol as a solvent, flow rate of 10 ml/min, UV detection at 256 nm), thereby obtaining three dehydro-products at retention times of 3.9 min, 9.1 min and 11.6 min. Instrumental analysis indicates that the product eluted at 9.1 min is E-tetradehydrocyclophenylalanylhistidyl (CE-ΔFΔH) of the formula (IV), the product eluted at 11.6 min is Z-tetradehydrocyclophenylalanylhistidyl (CZ-ΔFΔH) of the formula (V), and the product eluted at 30.1 min is dehydrocyclophenylalanylhistidyl (CFΔH) of the formula (VI).

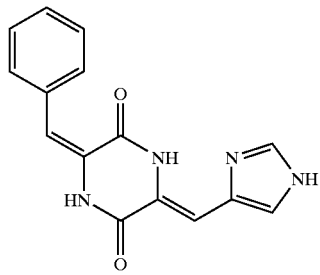
(IV)

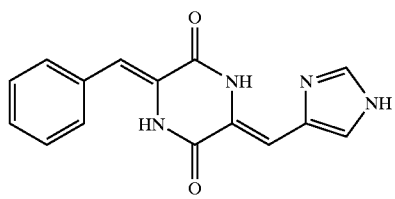
(V)

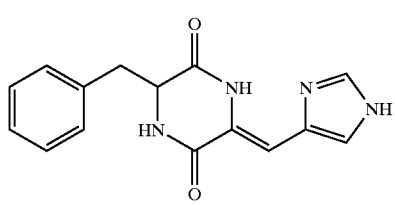
(VI)

The compound (V) has the following physicochemical data:

EIMS m/z: 280 (M$^+$, 100), 107 (36), 279 (29), 281 (18).

UV (MeOH) 1max, nm(e): 205 (14800), 257 (6500), 351 (27100).

$^1$H-NMR (500 MHz, CDCl$_3$):

δ 6.77, 1H, s

δ 7.02, 1H, s

δ 7.22, 1H, m

δ 7.33, 1H, t (J=7.3)

δ 7.37, 2H, d (J=7.3)

δ 7.43, 2H, dd (J=7.3, 7.3)

δ 7.75, 1H, s

δ 8.09, 1H, s

δ 9.30, 1H, br s

δ 11.91, 1H, s

EXAMPLE 3

A variety of dehydrodiketopiperazines were prepared from different diketopiperazines as substrates through dehydrogenation reactions using the enzyme of the present invention as follows.

TABLE 5

| Reaction mixture composition | |
| --- | --- |
| Dimethyl sulfoxide (DMSO) | 10% (v/v) |
| Sodium phosphate buffer (pH 8.0) | 5.2 mM |
| Dichlorophenolindophenol (DCIP) | 80 μM |
| Phenazine methosulfate (PMS) | 120 μM |
| Cell-free extract from Example 1 | q.s. |
| Substrate | 0.5 mM |
| Total | 0.5 ml |

The reaction mixture shown in Table 5 was used for the dehydrogenation reaction at 37° C. The reaction product was analyzed by HPLC and detected by UV absorbance at 256 nm. This method provided the following dehydro-products:

ΔCAF, ΔCFF, ΔCFG, ΔCFH, ΔCFL, CΔFL, CFΔL, ΔCFS, ΔCFV, ΔCFW, ΔCLW, ΔCLY, ΔCVY, ΔCWW, ΔCWY, ΔCDWY (W residue is D-form), and ΔPLH.

EXAMPLE 4

A variety of dehydrodiketopiperazines were prepared from different diketopiperazines as substrates through dehydrogenation reactions using the enzyme of the present invention as follows.

TABLE 6

| Reaction mixture composition | |
| --- | --- |
| Dimethyl sulfoxide (DMSO) | 10% (v/v) |
| Sodium phosphate buffer (pH 8.0) | 5.2 mM |
| Cell-free extract from Example 1 | q.s. |
| Substrate | 0.5 mg/ml |
| Total | 0.5 ml |

The reaction mixture shown in Table 6 was used for the dehydrogenation reaction at 37° C. The reaction product was analyzed by HPLC and detected by a photodiode array detector (multi-channel UV, 220 nm to 400 nm). This method provided the following dehydro-products:

ΔCΔH, ΔCAW, ΔCAY, ΔCD(OMe)D(OMe), ΔCDF, ΔCFG, ΔCFS, ΔCFV, ΔCFW, ΔCGL, ΔCGW, ΔCGY, ΔCHH, ΔCHW, ΔCHY, ΔCLP, ΔCLW, ΔCLY, ΔCMM, ΔCSY, ΔCVW, ΔCWW, ΔCWY, ΔCDWY (W residue is D-form), and ΔCD(OEt)G, wherein D(OMe) represents an aspartic acid having a methylated carboxyl group on its side chain (γ-position), and D(OEt) represents an aspartic acid having a ethylated carboxyl group on its side chain (γ-position).

EXAMPLE 5

A variety of dehydrodiketopiperazines were prepared from different diketopiperazines as substrates through dehydrogenation reactions using the enzyme of the present invention as follows.

The reaction procedures as described in Example 3 were repeated and an amount of dehydrogenation by the enzyme was determined based on a change in absorbance at 600 nm due to coenzyme. Table 7 shows the amount of dehydrogenation by the enzyme (i.e., a change in absorbance) for each substrate, which is expressed as a relative value (an absorbance for CFL was set to 100).

TABLE 7

Amount of dehydrogenation of each substrate by enzyme

| Substrate | Amount of dehydrogenation |
|---|---|
| CFL | 100 |
| CFH | 44 |
| CMM | 27 |
| CEE | 14 |
| CLY | 14 |
| CDD | 14 |

EXAMPLE 6

Dehydrogenase derived from *Streptomyces albulus* KO23, which requires diketopiperazine as its substrate, was purified according to the procedures as described in Example 1.

*Streptomyces albulus* KO23 was cultured in a mini jar containing 3 L culture medium to obtain 167.12 g of the cells. The cell-free extract was prepared from these cells as follows.

TABLE 8

Preparation of cell-free extract

| Conversion activity (units/ml) | Protein ($A_{280}$) (mg/ml) | Specific activity (units/mg) | Liquid volume (ml) | Total activity (units) |
|---|---|---|---|---|
| 0.684 | 14.2 | 0.0482 | 382 | 261.3 |

The resulting extract was subjected to DEAE-Sephacel anion exchange column chromatography.

| Column: | DEAE-Sephacel φ 2.6 cm × 30 cm |
|---|---|
| Flow rate: | 1 ml/min |
| Fraction size: | 10 ml |
| Sample: | 113 ml cell-free extract |

As a buffer, 10 mM sodium phosphate buffer (pH 8.0) containing 0.1 mM DTT was used. After the sample was adsorbed to the column, the column was washed with 360 ml buffer, and then eluted stepwise with 400 ml buffer containing 0.1 M NaCl, 410 ml buffer containing 0.3 M NaCl, and 600 ml buffer containing 0.5 M NaCl, thereby obtaining the following active fractions.

TABLE 9

Purification by DEAE-Sephacel anion exchange column chromatography

| Fraction | Conversion activity (units/ml) | Protein ($A_{280}$) (mg/ml) | Specific activity (units/mg) | Liquid volume (ml) | Total activity (units) |
|---|---|---|---|---|---|
| 50–56 | 0.179 | 1.42 | 0.126 | 70 | 12.5 |
| 57–71 | 0.240 | 2.56 | 0.0781 | 152 | 30.4 |

Fractions 50–56 having a higher specific activity were subjected to the subsequent Mono-Q column chromatography as follows.

| Column: | MonoQ HR 5/5 |
|---|---|
| Flow rate: | 1 ml/min |
| Fraction size: | 0.6 ml |
| Sample: | 4 × 1 ml DEAE-Sephacel fractions 50–56 diluted 2-fold with buffer |

As a buffer, 10 mM sodium phosphate buffer (pH 8.0) containing 0.1 mM DTT was used. After the sample was adsorbed to the column, the column was washed with the buffer for 4 minutes, and then eluted with 1 M NaCl-containing buffer using a linear gradient (25 min). The above procedures were repeated four times to obtain the following active fraction.

TABLE 10

Purification by MonoQ anion exchange column chromatography

| Conversion activity (units/ml) | Protein ($A_{280}$) (mg/ml) | Specific activity (units/mg) | Liquid volume (ml) | Total activity (units) |
|---|---|---|---|---|
| 0.0201 | 0.0376 | 0.646 | 7.2 | 0.145 |

The above active fraction was subjected to gel filtration chromatography (Superose 12) as follows.

| Column: | Superose 12 HR 10/30 |
|---|---|
| Flow rate: | 0.5 ml/min |
| Fraction size: | 0.25 ml |
| Sample: | MonoQ active fraction concentrated to 225 μl |

As a buffer, 10 mM sodium phosphate buffer (pH 8.0) containing 0.1 mM DTT and 0.3 M NaCl was used. Table 11 shows enzyme activity of each fraction. The most active fractions 13–16 were combined together and concentrated by ultrafiltration.

TABLE 11

Purification by Superose 12 gel filtration column chromatography

| Fraction | Conversion activity (units/ml) | Liquid volume (μL) | Total activity (units) |
|---|---|---|---|
| 11, 12 | 0.0737 | 100 | 7.37 |
| 13, 14 | 0.253 | 45 | 11.4 |
| 15, 16 | 0.184 | 45 | 8.28 |
| 17, 18 | 0.0526 | 80 | 4.21 |

The above active fraction was subjected to gel filtration chromatography (TSK G3000SWXL) with Waters LC Module1 as follows.

| Column: | TSK GEL G3000SWXL |
|---|---|
| Flow rate: | 0.5 ml/min |
| Sample: | Superose active fraction concentrated to 40 μl |

As a buffer, 100 mM sodium phosphate buffer (pH 7.5) containing 0.1 mM DTT and 0.3 M NaCl was used. The resulting active fractions were combined together and concentrated by ultrafiltration. Table 12 shows enzyme activity of the combined and concentrated fraction.

TABLE 12

Purification by TSK G3000SWXL gel filtration chromatography

| Activity (units) | Protein (A₂₈₀) (mg/ml) | Specific activity (units/mg) |
|---|---|---|
| 0.00224 | 0.00114 | 19.6 |

Table 13 shows enzyme activity in each step of the purification procedures and a final enzyme activity.

TABLE 13

Enzyme purification and specific activity

| Purification step | Enzyme activity (units) | Protein (mg) | Specific activity (units/mg) |
|---|---|---|---|
| Cell-free extract | 0.734 | 15.2 | 0.0482 |
| DEAE-Sephacel | 0.119 | 0.946 | 0.126 |
| Mono-Q | 0.0644 | 0.120 | 0.537 |
| Superose 12 | 0.00790 | 0.00799 | 0.989 |
| TSK G3000SW | 0.00224 | 0.000114 | 19.6 |

EXAMPLE 7

The reaction mixture shown in Table 14 was used for the enzymatic reaction using the enzyme of the present invention. Various diketopiperazines were used as substrates. The resulting enzymatic reaction mixture was tested for its inhibitory activity against embryo division of *Temnopleurus toreumaticus* without any purification of the reaction product. The test was carried out as described in The Journal of Antibiotics, Vol. 52, p. 1017 (1999). However, stages at which the first cleavage division occurs vary among sea urchins, so that inhibition of the cleavage division was observed after one hour of fertilization in this test using *Temnopleurus toreumaticus*. Concentration of the substrate added to the enzymatic reaction system was used as a criterion for inhibitor concentration because the reaction product was used for the test without any purification. The inhibition test for the embryo division of *Temnopleurus toreumaticus* started with the highest substrate concentration of 25 μg/ml, followed by serially diluted substrate concentrations. Table 15 shows the test results.

TABLE 14

Reaction mixture composition

| | |
|---|---|
| Dimethyl sulfoxide (DMSO) | 10% (v/v) |
| Sodium phosphate buffer (pH 8.0) | 5.2 mM |
| Cell-free extract from Example 1 | q.s. |
| Substrate | 0.5 mg/ml |
| Total | 0.2 ml |

TABLE 15

Inhibition test for cleavage division using the enzymatic reaction mixture

| | MIC (μg/ml) |
|---|---|
| CDF reaction product | >25 (80% inhibition at 25 μg/ml) |
| CFF reaction product | >25 (90% inhibition at 25 μg/ml) |
| CFV reaction product | 25 |
| CGL reaction product | >13 (70% inhibition at 13 μg/ml) |
| CHW reaction product | 13 |
| CLY reaction product | >13 (60% inhibition at 13 μg/ml) |
| CWY reaction product | 6.3 |

EXAMPLE 8

Physiological activity of each dehydrodiketopiperazine will be described below. Each dehydrodiketopiperazine was tested for its inhibitory activity against cleavage division of *Hemicentrotus pulcherrimus*, *Scaphechinus mirabilis* and *Temnopleurus toreumaticus* as a cell division inhibitory activity. The test was carried out as described in The Journal of Antibiotics, Vol. 52, p. 1017 (1999). However, stages at which the first cleavage division occurs vary among sea urchins, so that inhibition of the cleavage division was observed after 4 hours of fertilization in the tests using *Hemicentrotus pulcherrimus* and *Scaphechinus mirabilis*, and after one hour of fertilization in the test using *Temnopleurus toreumaticus*, respectively. Table 16 shows the test results.

TABLE 16

Inhibition test for cell division using dehydrophenylahistin and related compounds

| | Compound | Scaphechinus mirabilis | Temnopleurus toreumaticus | Hemicentrotus pulcherrimus |
|---|---|---|---|---|
| Example 1 | dehydrophenylahistin | 0.0061 | 0.0061 | 0.00038 |
| Example 2 | (Z,Z)-tetradehydro-CFH | 1.6 | 1.6 | 0.78 |
| Comparison 1 | (−)-phenylahistin | 1.6 | 0.2 | 0.39 |
| Comparison 2 | (+)-phenylahistin | >13* | 6.3 | 13 |
| Comparison 3 | albonoursin | >13* | >25* | 6.3 |
| Comparison 4 | CFH | >25* | >25* | >25* |

*no activity at the indicated concentration

Dehydrophenylahistin has MIC of 0.0061 µg/ml for cell division of *Scaphechinus mirabilis* and *Temnopleurus toreumaticus*, and MIC of 0.00038 µg/ml for cell division of *Hemicentrotus pulcherrimus*, respectively. Dehydrophenylahistin exhibits 250-fold to 1000-fold inhibitory activity when compared with non-dehydrogenated (−)-phenylahistin. (Z,Z)-tetradehydro-CFH obtained by dehydrogenation of CFH exhibits 15-fold or more inhibitory activity when compared with CFH. In any case, a variety of dehydrodiketopiperazines including dehydrophenylahistin and (Z,Z)-tetradehydro-CFH were shown to have the cell division inhibitory activity, indicating that the dehydrodiketopiperazines are useful as cell division inhibitors and antitumor agents.

Formulation Example 1

Formulation for Injection or Drip Infusion

One milligram of dehydrophenylahistin and 5 g of glucose powder were aseptically distributed to each vial. Each vial was sealed under an inert gas such as nitrogen or helium, and then stored in a cool dark place. Before use, ethanol was added to each vial to dissolve its content, followed by addition of 100 ml 0.85% physiological saline to produce a formulation for intravenous injection. The resulting formulation is intravenously injected or infused in an amount of 10 to 100 ml per day depending on symptoms.

Formulation Example 2

Formulation for Injection or Drip Infusion

The procedures as described in Formulation example 1 were repeated to produce a formulation for intravenous injection containing 0.2 mg dehydrophenylahistin, which may be used for treatment of mild cases. The resulting formulation is intravenously injected or infused in an amount of 10 to 100 ml per day depending on symptoms.

Formulation Example 3

Granules

One hundred milligrams of dehydrophenylahistin, 98 g of lactose and 1 g of hydroxypropylcellulose were mixed well, granulated by standard techniques, dried well and passed through a mesh, thereby obtaining granules suitable for packaging in a bottle or heat seal. The resulting granules are orally administered in an amount of 100 to 1000 mg per day depending on symptoms.

All publications, patents and patent applications cited herein are incorporated herein by reference in their entirety.

INDUSTRIAL APPLICABILITY

The present invention provides a cell division inhibitor having stronger cell cycle inhibitory activity, particularly antitumor activity, and an enzyme usable for the production thereof.

What is claimed is:

1. A cell division inhibitor comprising, as an active ingredient, a compound of formula (II) or an E form thereof, or pharmaceutically acceptable salt thereof:

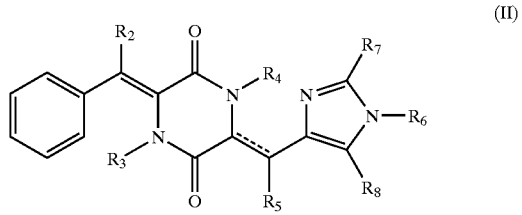

wherein
$R_1$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_1$ may be branched or cyclized, or may comprise a heteroatom, and further $R_1$ may be one atom or group, or at most 5 identical or different atoms or groups, and the atoms or groups may mutually form a ring;

$R_2$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_2$ may be branched or cyclized, or may comprise a heteroatom;

each of $R_3$ and $R_4$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;

$R_5$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_5$ may be branched or cyclized, or may comprise a heteroatom;

$R_6$ is hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain of $R_6$ may be branched or cyclized, or may comprise a heteroatom;

each of $R_7$ and $R_8$ is independently hydrogen, halogen, $C_{1-25}$ alkyl, $C_{2-25}$ alkenyl, $C_{2-25}$ alkynyl, $C_{1-25}$ alkoxy, aralkyl, hydroxyl, amino, nitro or aryl, which may be substituted with other substituent(s), and a part of the carbon chain may be branched or cyclized, or may comprise a heteroatom;

$R_2$ and $R_3$ may form a ring;

$R_4$ and any of $R_5$, $R_6$, $R_7$ and $R_8$ may form a ring;

the bond depicted by a solid line and dashed line represents a carbon—carbon single bond or a carbon—carbon double bond;

at least one of said groups may have a protecting group capable of decomposing in vivo.

2. The cell division inhibitor according to claim 1 wherein, in said formula (II), the bond depicted by a solid line and dashed line is a carbon—carbon double bond.

3. The cell division inhibitor according to claim 2 wherein, in said formula (II), at least one of $R_7$ and $R_8$ is 1,1-dimethyl-2-propenyl.

4. The cell division inhibitor according to claim 1 which is an antitumor agent.

5. A compound of formula (II) or an E form thereof, or pharmaceutically acceptable salt thereof:

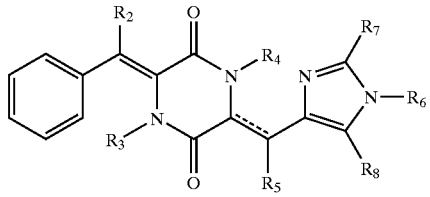

(II)

wherein
R$_1$ is hydrogen, halogen, C$_{1-25}$ alkyl, C$_{2-25}$ alkenyl, C$_{2-25}$ alkynyl, C$_{1-25}$ alkoxy, aralkyl, hydroxyl, amino, nitro or aryl, which may be substituted with other substituent(s), and a part of the carbon chain of R$_1$ may be branched or cyclized, or may comprise a heteroatom, and further R$_1$ may be one atom or group, or at most 5 identical or different atoms or groups, and the atoms or groups may mutually form a ring;

R$_2$ is hydrogen, halogen, C$_{1-25}$ alkyl, C$_{2-25}$ alkenyl, C$_{2-25}$ alkynyl, C$_{1-25}$ alkoxy, aralkyl, hydroxyl, amino, nitro or aryl, which may be substituted with other substituent(s), and a part of the carbon chain of R$_2$ may be branched or cyclized, or may comprise a heteroatom;

each of R$_3$ and R$_4$ is independently hydrogen, halogen, C$_{1-25}$ alkyl, C$_{2-25}$ alkenyl, C$_{2-25}$ alkynyl, C$_{1-25}$ alkoxy, aralkyl, hydroxyl, amino, nitro or aryl, which may be substituted with other substituent(s), and a part of the carbon chain may be branched or cyclized, or may comprise a heteroatom;

R$_5$ is hydrogen, halogen, C$_{1-25}$ alkyl, C$_{2-25}$ alkenyl, C$_{2-25}$ alkynyl, C$_{1-25}$ alkoxy, aralkyl, hydroxyl, amino, nitro or aryl, which may be substituted with other substituent(s), and a part of the carbon chain of R$_5$ may be branched or cyclized, or may comprise a heteroatom;

R$_6$ is hydrogen, halogen, C$_{1-25}$ alkyl, C$_{2-25}$ alkenyl, C$_{2-25}$ alkynyl, C$_{1-25}$ alkoxy, aralkyl, hydroxyl, amino, nitro or aryl, which may be substituted with other substituent(s), and a part of the carbon chain of R$_6$ may be branched or cyclized, or may comprise a heteroatom;

each of R$_7$ and R$_8$ is independently hydrogen, halogen, C$_{1-25}$ alkyl, C$_{2-25}$ alkenyl, C$_{2-25}$ alkynyl, C$_{1-25}$ alkoxy, aralkyl, hydroxyl, amino, nitro or aryl, which may be substituted with other substituent(s), and a part of the carbon chain may be branched or cyclized, or may comprise a heteroatom;

R$_2$ and R$_3$ may form a ring;

R$_4$ and any of R$_5$, R$_6$, R$_7$ and R$_8$ may form a ring;

the bond depicted by a solid line and dashed line represents a carbon—carbon single bond or a carbon—carbon double bond;

at least one of said groups may have a protecting group capable of decomposing in vivo.

6. The compound of claim 5, wherein each of R$_2$, R$_3$, R$_4$, R$_5$, R$_6$ and R$_7$ is a hydrogen, R$_8$ is 1,1-dimethyl-2-propenyl, and the bond depicted by a solid line and a dashed line represents a carbon—carbon double bond.

7. The compound of claim 5, wherein each of R$_2$, R$_3$, R$_4$, R$_5$, R$_6$, R$_7$ and R$_8$ is a hydrogen and the bond depicted by a solid line and a dashed line represents a carbon—carbon double bond.

8. The cell divisional inhibitor according to claim 1, wherein each of R$_2$, R$_3$, R$_4$, R$_5$, R$_6$ and R$_7$ is a hydrogen, R$_8$ is 1,1-dimethyl-2-propenyl, and the bond depicted by a solid line and a dashed line represents a carbon—carbon double bond.

9. The cell division inhibitor according to claim 1, wherein each of R$_2$, R$_3$, R$_4$, R$_5$, R$_6$, R$_7$ and R$_8$ is a hydrogen and the bond depicted by a solid line and a dashed line represents a carbon—carbon double bond.

* * * * *

UNITED STATES PATENT AND TRADEMARK OFFICE
CERTIFICATE OF CORRECTION

| | | |
|---|---|---|
| PATENT NO. | : 6,972,289 B1 | Page 1 of 1 |
| APPLICATION NO. | : 10/181786 | |
| DATED | : December 6, 2005 | |
| INVENTOR(S) | : Kanzaki et al. | |

It is certified that error appears in the above-identified patent and that said Letters Patent is hereby corrected as shown below:

Column 22, lines 1-10 and column 23, lines 5-14, the chemical structure of formula (II) should appear as follows:

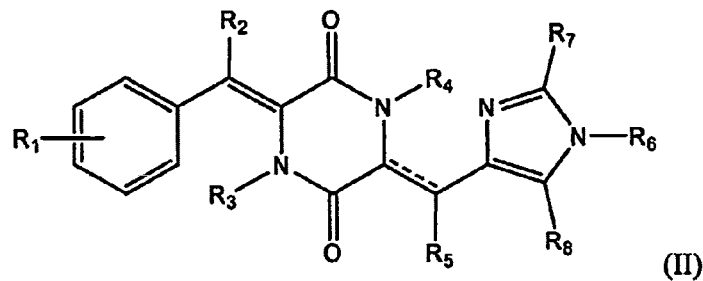

(II)

Signed and Sealed this

Seventh Day of November, 2006

JON W. DUDAS
*Director of the United States Patent and Trademark Office*